(12) United States Patent
Hohlweg et al.

(10) Patent No.: US 6,214,816 B1
(45) Date of Patent: Apr. 10, 2001

(54) HETEROCYCLIC COMPOUNDS

(75) Inventors: Rolf Hohlweg, Kvistgaard; Tine Krogh Jørgensen, Herlev; Knud Erik Andersen, Brøndby; Uffe Bang Olsen, Vallensbæk, all of (DK); Zdeněk Polivka, Praha; Karel Sindelar, Praha, both of (CZ)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/266,236

(22) Filed: Mar. 10, 1999

Related U.S. Application Data

(60) Provisional application No. 60/078,954, filed on Mar. 23, 1998.

(30) Foreign Application Priority Data

Mar. 17, 1998 (DE) ................................................. 0366/98

(51) Int. Cl.⁷ .................... C07D 401/06; C07D 403/06; C07D 409/06; A61K 31/55; A61P 29/00
(52) U.S. Cl. .................... 514/183; 514/217; 514/228.2; 514/232.8; 514/253.03; 514/297; 540/479; 540/591; 540/592; 544/60; 544/126; 544/361; 546/104
(58) Field of Search .................... 514/183, 217, 514/228.2, 232.8, 253.03, 297; 540/479, 591, 592; 544/60, 126, 361; 546/104

(56) References Cited

U.S. PATENT DOCUMENTS

| | | | |
|---|---|---|---|
| 4,017,621 | * | 4/1977 | Takashima et al. ................. 514/217 |
| 4,085,210 | * | 4/1978 | Katsube et al. ..................... 514/183 |
| 4,169,146 | * | 9/1979 | Katsube et al. ..................... 514/238.8 |

FOREIGN PATENT DOCUMENTS

| | | |
|---|---|---|
| 25 55 351 | 6/1976 | (DE) . |
| 26 00 358 | 7/1976 | (DE) . |
| 1013909 | 12/1965 | (GB) . |
| 1043158 | 9/1966 | (GB) . |
| WO 96/31497 | 10/1996 | (WO) . |
| WO 96/31498 | 10/1996 | (WO) . |
| WO 96/31500 | 10/1996 | (WO) . |

* cited by examiner

*Primary Examiner*—Mukund J. Shah
*Assistant Examiner*—Thomas McKenzie

(74) *Attorney, Agent, or Firm*—Steve T. Zelson, Esq.; Carol E. Rozek, Esq.

(57) ABSTRACT

The compounds are N-substituted azaheterocyclic compounds of formula I

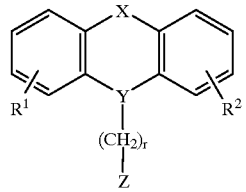

(I)

wherein $R^1$ and $R^2$ independently are hydrogen, halogen, trifluoromethyl, hydroxy, $C_{1-6}$-alkyl or $C_{1-6}$-alkoxy; and Y is >N—$\underline{CH_2}$— wherein only the underscored atom participates in the ring system; and X is —C($R^6R^7$)—, —$CH_2CH_2$—, —CH=CH—$CH_2$—, —$CH_2$—CH=CH—, —$CH_2$—(C=O)—, —(C=O)—$CH_2$—, —$CH_2CH_2CH_2$—, —CH=CH—, CH($R^{10}$)$CH_2$—, —$CH_2$CH($R^{10}$) or —(C=O)— wherein $R^6$ and $R^7$ independently are hydrogen or $C_{1-6}$-alkyl and wherein $R^{10}$ is $C_{1-6}$-alkyl or phenyl; and r is 0, 1 or 2; and Z is selected from

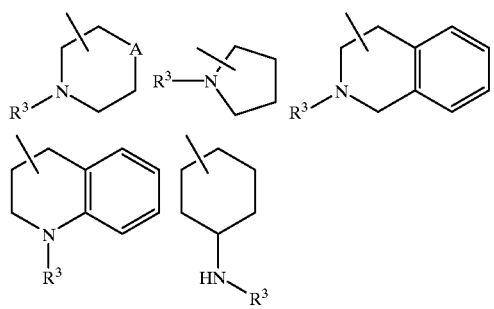

wherein A is —$CH_2$—, —O—, —S— or —N($R^5$)— wherein $R^5$ is H or $C_{1-6}$-alkyl; and $R^3$ is —$(CH_2)_p$COR$^4$ wherein p is 1, 2, 3 or 4 and $R^4$ is OH, $NH_2$, NHOH or $C_{1-6}$-alkoxy; or a pharmaceutically acceptable salt thereof. These compounds are useful for treating painful, hyperalgesic and/or inflammatory conditions in which C-fibers play a pathophysiological role by eliciting neurogenic pain or inflammation. They are also useful for treating indications caused by or related to the secretion and circulation of insulin antagonizing peptides, e.g., non-insulin-dependent diabetes mellitus (NIDDM) and ageing-associated obesity.

18 Claims, No Drawings

HETEROCYCLIC COMPOUNDS

CROSS-REFERENCE TO RELATED APPLICATIONS

This application claims priority under 35 U.S.C. 119 of Danish application serial no. 0366/98 filed Mar. 17, 1998 and U.S. Provisional application serial No. 60/078,954 filed Mar. 23, 1998, the contents of which are fully incorporated herein by reference.

FIELD OF INVENTION

The present invention relates to novel N-substituted azaheterocyclic compounds in which a substituted alkyl chain forms part of the N-substituent or salts thereof, to methods for their preparation, to compositions containing them, to the use of the compounds for preparing compositions for the clinical treatment of painful, hyperalgesic and/or inflammatory conditions in which C-fibres play a pathophysiological role, and to methods of treating said painful, hyperalgesic and/or inflammatory conditions. The invention also relates to the use of the present compounds for reducing blood glucose and/or inhibit the secretion, circulation or effect of insulin antagonizing peptides like CGRP or amylin, the present compounds being known to interfere with neuropeptide containing C-fibres. Hence the present compounds can be used in the treatment of non-insulin-dependent diabetes mellitus (NIDDM) in order to improve the glucose tolerance as well as ageing-associated obesity.

BACKGROUND OF INVENTION

The nervous system exerts a profound effect on the inflammatory response. Antidromic stimulation of sensory nerves results in localised vasodilation and increased vascular permeability (Janecso et al. Br. J. Pharmacol. 1967, 31, 138–151), and a similar response is observed following injection of peptides known to be present in sensory nerves. From this and other data it is postulated that peptides released from sensory nerve endings mediate many inflammatory responses in tissues like skin, joint, urinary tract, eye, meninges, gastro-intestinal and respiratory tracts. Hence inhibition of sensory nerve peptide release and/or activity may be useful in treatment of for example arthritis, dermatitis, rhinitis, asthma, cystitis, gingivitis, thrombophlelitis, glaucoma, gastrointestinal diseases or migraine.

Furthermore, the fact that the C-fibers innervate the liver, the intestines and the pancreas suggests that they control various function. The peptidergic innervation has been shown to control glucose tolerance in rodents (Karlsson et al. Am. J. Physiol. 267, R1071–R1077, 1994, Guillot et al. Life Sci. 969–977, 1996).

Further, the potent effects of CGRP on skeletal muscle glycogen synthase activity and muscle glucose metabolism, together with the notion that this peptide is released from the neuromuscular junction by nerve excitation, suggest that CGRP may play a physiological role in skeletal muscle glucose metabolism by directing the phosphorylated glucose away from glycogen storage and into the glycolytic and oxidative pathways (Rossetti et al. Am. J. Physiol. 264, E1–E10, 1993). This peptide may represent an important physiological modulator of intracellular glucose trafficking in physiological conditions, such as exercise, and may also contribute to the decreased insulin action and skeletal muscle glycogen synthase in pathophysiological conditions like NIDDM or ageing-associated obesity (Melnyk et al. Obesity Res. 3, 337–344, 1995) where circulating plasma levels of CGRP are markedly increased. Hence inhibition of release and/or activity of the neuropeptide CGRP and other sensory neuropeptides may be useful in the treatment of insulin resistance related to type 2 diabetes or ageing.

In U.S. Pat. Nos. 4,383,999 and 4,514,414 and in EP 236342 as well as in EP 231996 some derivatives of N-(4,4-disubstituted-3-butenyl)azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. Further, in WO 9107389 and WO 9220658, N-substituted azacyclic carboxylic acids are claimed as GABA uptake inhibitors. EP 221572 claims that 1-aryloxyalkylpyridine-3-carboxylic acids are inhibitors of GABA uptake. WO 9518793 discloses N-substituted azaheterocyclic carboxylic acids and esters thereof.

SUMMARY OF THE INVENTION

The present invention relates to compounds of the general formula 1, wherein X, Y, $R^1$, $R^2$, Z and r are as defined in the detailed part of the present description.

The present compounds are useful for the treatment, prevention, elimination, alleviation or amelioration of an indication related to all painful, hyperalgesic and/or inflammatory conditions in which C-fibres play a pathophysiological role, e.g. neurogenic pain, neurogenic inflammation, migraine, neuropathy, itching and rheumatoid arthritis, as well as indications caused by or related to the secretion and circulation of insulin antagonising peptides and other peptides derived from the sensory nervous system, e.g. non-insulin-dependent diabetes mellitus (NIDDM), insulin resistance and ageing-associated obesity.

In another aspect, the present invention includes within its scope pharmaceutical compositions comprising, as an active ingredient, at least one of the compounds of the general formula I or a pharmaceutically acceptable salt thereof together with a pharmaceutically acceptable carrier or diluent.

In another aspect of the present invention there is provided a method of treating painful, hyperalgesic and/or inflammatory conditions in which C-fibres play a pathophysiological role, e.g. neurogenic pain, neurogenic inflammation, migraine, neuropathy, itching and rheumatoid arthritis, as well as a method of treating indications caused by or related to the secretion and circulation of insulin antagonising peptides, e.g. non-insulin-dependent diabetes mellitus (NIDDM), insulin resistance and ageing-associated obesity.

The method of treatment may be described as the treatment, prevention, elimination, alleviation or amelioration of one of the above indications, which comprises the step of administering to the said subject a neurologically effective amount of a compound of the invention, or a pharmaceutically acceptable salt thereof.

A further aspect of the invention relates to the use of a compound of the present invention for the preparation of a pharmaceutical composition for the treatment of all painful, hyperalgesic and/or inflammatory conditions in which C-fibres play a pathophysiological role, e.g. neurogenic pain, neurogenic inflammation, migraine, neuropathy, itching and rheumatoid arthritis, as well as for the treatment of indications caused by or related to the secretion and circulation of insulin antagonising peptides and other peptides derived from the sensory nervous system, e.g. non-insulindependent diabetes mellitus (NIDDM), insulin resistance and ageing-associated obesity.

Further objects will become apparent from the following description.

DETAILED DESCRIPTION OF THE INVENTION

Accordingly, the present invention relates to novel N-substituted azaheterocyclic compounds of the general formula I

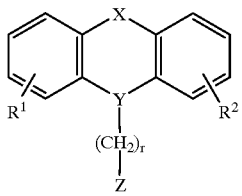

(I)

wherein $R^1$ and $R^2$ independently are hydrogen, halogen, trifluoromethyl, hydroxy, $C_{1-6}$-alkyl or $C_{1-6}$-alkoxy; and Y is >N—$CH_2$—, >C=CH— or >CH—$CH_2$— wherein only the underscored atom participates in the ring system; and X is ortho-phenylene, —O—, —S—, —C($R^6R^7$)—, —$CH_2CH_2$—, —CH=CH—$CH_2$—, —$CH_2$—CH=CH—, —$CH_2$—(C=O)—, —(C=O)—$CH_2$—, —$CH_2CH_2CH_2$—, —CH=CH—, —N($R^8$)—(C=O)—, —(C=O)—N($R^8$)—, —O—$CH_2$—O—, —$OCH_2O$—, —S—$CH_2$—, —$CH_2$—S—, —($CH_2$)N($R^8$)—, —N($R^8$)($CH_2$)—, —N($CH_3$)$SO_2$—, —$SO_2$N($CH_3$)—, CH($R^{10}$)$CH_2$—, —$CH_2$CH($R^{10}$), —(C=O)—, —N($R^9$)— or —(S=O)— wherein $R^6$, $R^7$, $R^8$ and $R^9$ independently are hydrogen or $C_{1-6}$-alkyl and wherein $R^{10}$ is $C_{1-6}$-alkyl or phenyl; and r is 0, 1 or 2; and Z is selected from

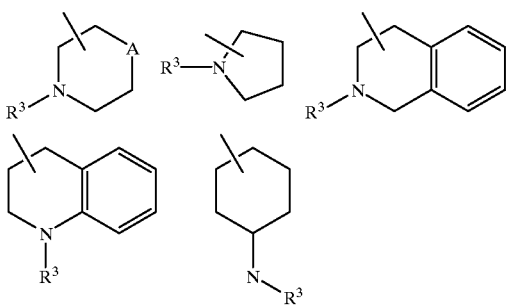

wherein A is —$CH_2$—, —O—, —S— or —N($R^5$)— wherein $R^5$ is H or $C_{1-6}$-alkyl; and $R^3$ is —($CH_2$)$_m$OH or —($CH_2$)$_p$$COR^4$ wherein m and p independently are 1, 2, 3 or 4 and $R^4$ is OH, $NH_2$, NHOH or $C_{1-6}$-alkoxy; or a pharmaceutically acceptable salt thereof.

The compounds of formula I may exist as geometric and optical isomers and all isomers, as sepavreted, pure or partially purified stereoisomers or racemic mixtures thereof are included in the scope of the invention. Isomers may be separated by means of standard methods such as chromatographic techniques or fractional crystallisation of suitable salts.

Preferably, the compounds of formula I exist as the individual geometric or optical isomers.

The compounds according to the invention may optionally exist as pharmaceutically acceptable acid addition salts, metal salts or, optionally alkylated, ammonium salts.

Examples of such salts include inorganic and organic acid addition salts such as hydrochloride, hydrobromide, sulphate, phosphate, acetate, fumarate, maleate, citrate, lactate, tartrate, oxalate or similar pharmaceutically acceptable inorganic or organic acid addition salts. Further examples of pharmaceutically acceptable inorganic or organic acid addition salts include the pharmaceutically acceptable salts listed in *Journal of Pharmaceutical Science*, 66, 2 (1977) which are known to the skilled artisan.

Also included are the hydrates of the above mentioned acid addition salts which the present compounds are able to form.

The acid addition salts may be obtained as the direct products of compound synthesis. In the alternative, the free base may be dissolved in a suitable solvent containing the appropriate acid, and the salt isolated by evaporating the solvent or by precipitation or crystallisation.

The compounds of formula I may be administered in a pharmaceutically acceptable acid addition salt form or where possible as a metal or a lower alkylammonium salt. Such salt forms exhibit approximately the same order of activity as the free base forms.

In the above structural formula and throughout the present specification, the following terms have the indicated meaning:

The terms "$C_{1-6}$-alkyl" as used herein, alone or in combination, refers to a straight or branched, saturated hydrocarbon chain having 1 to 6 carbon atoms. Examples of such groups include, but are not limited to, methyl, ethyl, n-propyl, iso-propyl, n-butyl, sec-butyl, iso-butyl, tert-butyl, n-pentyl, iso-pentyl, 2-methylbutyl, 3-methylbutyl, n-hexyl, iso-hexyl, 4-methylpentyl, neopentyl, 1,2-dimethylpropyl, 2,2-dimethylpropyl, 1,2,2-trimethylpropyl and the like.

The term "halogen" means fluorine, chlorine, bromine or iodine.

The term "$C_{1-6}$-alkoxy" as used herein, alone or in combination is intended to include those $C_{1-6}$-alkyl groups of the designated length in either a linear or branched or cyclic configuration linked through an ether oxygen having its free valence bond from the ether oxygen. Examples of linear alkoxy groups are methoxy, ethoxy, propoxy, butoxy, pentoxy and hexoxy. Examples of branched alkoxy are isoprpoxy, sec-butoxy, tert-butoxy, isopentoxy and isohexoxy. Example of cyclic alkoxy are cyclopropyloxy, cyclobutyloxy, cyclopentyloxy and cyclohexyloxy.

In a preferred embodiment of the invention $R^1$ and $R^2$ are selected from hydrogen, halogen, trifluoromethyl or $C_{1-6}$-alkyl. Preferably $R^1$ and $R^2$ are hydrogen.

In another preferred embodiment of the invention X is selected from —S—, —$CH_2CH_2$—, —CH=CH—, —O—$CH_2$—, —$CH_2$—O—, —$OCH_2O$—, —S—$CH_2$— or —$CH_2$—S—. Preferably X is —$CH_2CH_2$—.

In another preferred embodiment of the invention Y is >N—$CH_2$—.

In another preferred embodiment of the invention r is 0, 1 or 2.

In another preferred embodiment of the invention Z is selected from

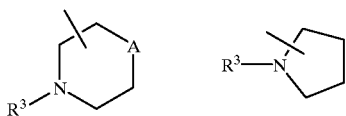

wherein A is —CH$_2$— or —O—.

In yet another preferred embodiment of the invention R$^3$ is —(CH$_2$)$_p$COOH wherein p is 1, 2, 3 or 4.

Preferred compounds of the present invention include:

3-(3-(10,11-Dihydro-5H-dibenzo[b,f]azepin-5-ylmethyl)-pyrrolidin-1-yl)-propionic acid;

(2-(2-(10,11-Dihydro-5H-dibenzo[b,f]azepin-5-ylmethyl)-morpholin-4-yl)-acetic acid;

(3-(10,11-Dihydro-5H-dibenz[(b,f]azepin-5-ylmethyl)-1-piperidyl)acetic acid;

or a pharmaceutically acceptable salt thereof.

Further preferred compounds of the present invention include:

(2-(3-(10,11-Dihydro-5H-dibenz[b,f]azepin-5-yl)-1-propyl)-1-piperidine)acetic acid;

(4-((10,11-Dihydro-5H-dibenz[b,f]azepin-5-yl)methyl)-1-piperidine)propionic acid;

or a pharmaceutically acceptable salt thereof.

It has been demonstrated that the novel compounds of formula I inhibit neurogenic inflammation which involves the release of neuropeptides from peripheral and central endings of sensory C-fibres. Experimentally this can be demonstrated in animal models of histamine induced paw oedema Amann et al. (Europ. J. Pharmacol. 279, 227–231, 1995) in which the novel compounds of formula I exhibit a potent inhibitory effect. Compounds of formula I may be used to treat all painful, hyperalgesic and/or inflammatory conditions in which C-fibres play a pathophysiological role by eliciting neurogenic pain or inflammation, i.e.:

Acutely painful conditions exemplified by migraine, post-operative pain, burns, bruises, post-herpetic pain (Zoster) and pain as it is generally associated with acute inflammation; chronic, painful and/or inflammatory conditions exemplified by various types of neuropathy (diabetic, post-traumatic, toxic), neuralgia, rheumatoid arthritis, spondylitis, gout, inflammatory bowel disease, prostatitis, cancer pain, chronic headache, coughing, asthma, itching, chronic pancreatitis, inflammatory skin disease including psoriasis and autoimmune dermatoses, osteoporotic pain.

Further, it has been demonstrated that the compounds of general formula I lower the glucose levels in diabetic rodents (ob/ob mice and diabetic fat Zucker rats) as well as improve the glucose tolerance and that this may result from the reduced release of CGRP from peripheral nervous endings and other peptides derived from the sensory nervous system. Hence the compounds of general formula I may be used in the treatment of NIDDM, insulin resistance as well as ageing-associated obesity. Experimentally this can be demonstrated by the administration of histamine chloride icv into NMRI mice with previous treatment ip of a compound of formula I.

The compounds of formula I may be prepared by the following method A:

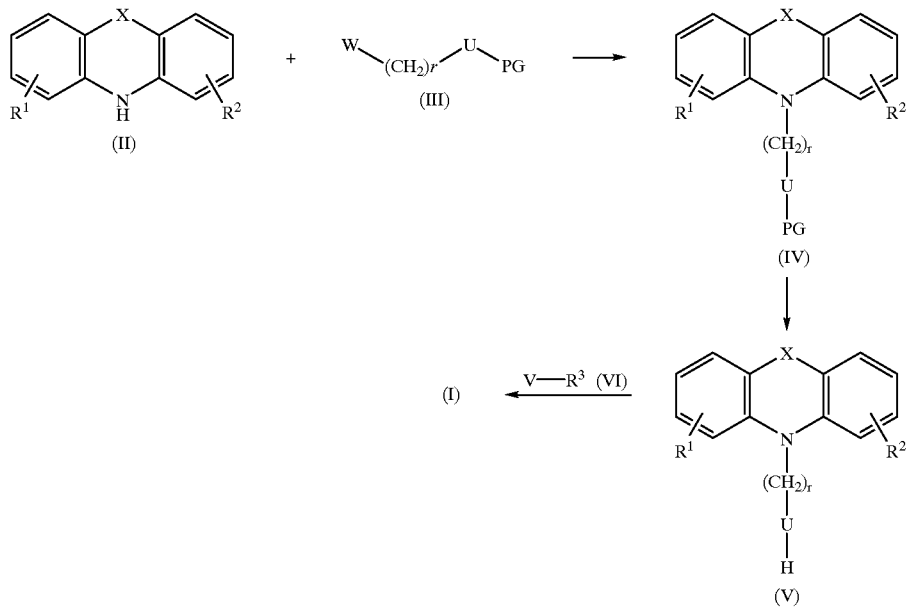

A compound of formula II wherein R$^1$, R$^2$ and X are as defined above may be reacted with a compound of formula III wherein r is as defined above, W is a suitable leaving group such as halogen, p-toluene sulphonate or mesylate, PG is a suitable N-protecting group, e.g. benzyl, and U is selected from

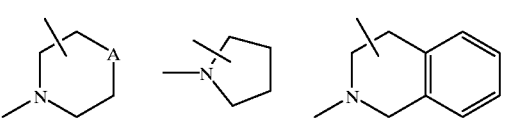

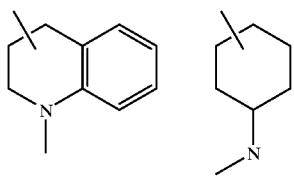

wherein A is as defined above, to form a compound of formula IV wherein $R^1$, $R^2$, X, r, U and PG are as defined above. This alkylation reaction may be carried out in a solvent such as N,N-dimethylformamide, acetone, dibutylether, 2-butanone, tetrahydrofuran (THF), dioxane or toluene in the presence of a base e.g. sodium hydride and a catalyst, e.g. an alkali metal iodide at a temperature up to reflux temperature for the solvent used for e.g. 1 to 120 h. The compound of formula IV may be N-deprotected, e.g. debenzylated to give a compound of formula V wherein $R^1$, $R^2$, X, r and U are as defined above. The debenzylation e.g. 1 to 120 h. If esters have been prepared in which $R^4$ is alkoxy, compounds of formula I wherein $R^4$ is OH may be prepared by hydrolysis of the ester group, preferably at room temperature in a mixture of an aqueous alkali metal hydroxide and an alcohol such as methanol or ethanol, for e.g. about 0.5 to 48 h.

Compounds of formulas II, III and VI may readily be prepared by methods familiar to those skilled in the art.

Alternatively, the compounds of formula I may be prepared by the following method B:

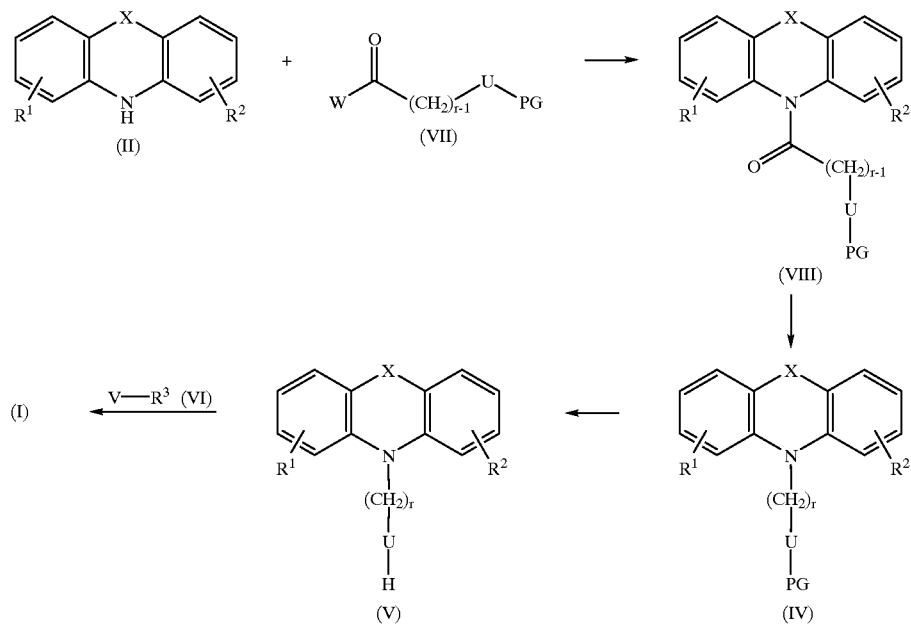

reaction may be carried out in a solvent or a mixture of solvents such as methanol, ethanol or toluene in the presence a catalyst, e.g. Pd/C under a hydrogen atmosphere. The compound of formula V may be N-alkylated with a compound of formula VI wherein $R^3$ is as defined above and V is a suitable leaving group such as halogen, p-toluene sulphonate or mesylate, to give a compound of formula I. This alkylation reaction may be carried out in a solvent such as N,N-dimethylformamide, acetone, dibutylether, 2-butanone, tetrahydrofuran (THF), dioxane or toluene in the presence of a base e.g. potassium carbonate or sodium hydride and a catalyst, e.g. an alkali metal iodide at a temperature up to reflux temperature for the solvent used for A compound of formula II wherein $R^1$, $R^2$ and X are as defined above may be reacted with a compound of formula VII wherein r is as defined above, W is a suitable leaving group such as halogen, p-toluene sulphonate or mesylate, PG is a suitable N-protecting group, e.g. benzyl, and U is selected from

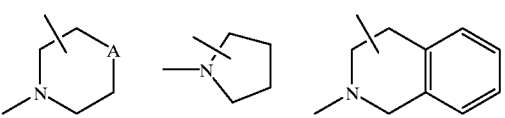

-continued

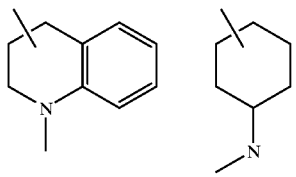

wherein A is as defined above, to form a compound of formula VII wherein $R^1$, $R^2$ X, r, U and PG are as defined above. This acylation reaction may be carried out in a solvent such as N,N-dimethylformamide, acetonitrile, acetone, 2-butanone or toluene in the presence of an assisting agent or base such as triethylamine or N,N-dimethylaniline at a temperature up to reflux temperature for the solvent used for e.g. 1 to 120 h. The compound of formula VIII may be reduced to give a compound of formula IV wherein $R^1$, $R^2$, X, r, U and PG are as defined above. The reduction may take place in a solvent such as tetrahydrofuran using sodium boron hydride and boron trifluoride ethyl etherate. The compound of formula IV may be N-deprotected, e.g. debenzylated to give a compound of formula V wherein $R^1$, $R^2$, X, r and U are as defined above. The debenzylation reaction may be carried out in a solvent or a mixture of solvents such as methanol, ethanol or toluene in the presence of a catalyst, e.g. Pd/C under a hydrogen atmosphere. The compound of formula V may be transformed to a compound of formula I as described under method A.

Compounds of formulas II, VII and VI may readily be prepared by methods familiar to those skilled in the art.

PHARMACOLOGICAL METHODS

I. Histamine Induced Paw Oedema

The rat histamine paw oedema test was performed essentially as described by Amann et al. (Europ. J. Pharmacol. 279, 227–231, 1995). In brief 250–300 g male Sprague-Dawley rats were anaesthetized with pentobarbital sodium, and placed on a 32 degree Celsius heated table. Ten minutes later histamine (50 micoliter, 3 mg/ml) was injected in the right hind paw and 20 minutes hereafter the paw swelling was determined by water plethysmography (Ugo Basile). Test compounds were administered intraperitoneally at 15 minutes before the anaesthetics.

II. Histamine Induced Hyperglycemia in Mice

Conscious unfasted 25 g male NMRI mice are administered histamine chloride (90 nmol) icv according to the method of Nishibori et al. (J. Pharmacol. Exp. Therap. 241, 582–286, 1987). Blood glucose is determined at time 0 and 40 min after the histamine injection. Test compounds are administered at 1.0 mg/kg ip 30 min before the histamine injection, and % inhibition refers to the capacity of the compounds to inhibit the histamine induced blood glucose rise.

III. Reduced Release of CGRP ob/ob female mice, 16 weeks of age, where injected glucose (2 g/kg) subcutaneously. At times hereafter blood glucose was determined in tail venous blood by the glucose oxidase method. At the end of the study the animals were decapitated and trunck blood collected. Immunoreactive CGRP was determined in plasma by radio-immuno-assay. Two groups of animals were used. The one group was vehicle treated, whereas the other group received a compound of formula I via drinking water (100 mg/l) for five days before the test.

Values for inhibition of histamine induced oedema response for a representative compound is listed in table I.

TABLE I

Inhibition of histamine induced paw oedema at 1.0 mg/kg

| Example no. | % inhibition |
|---|---|
| 01 | 56 |

PHARMACEUTICAL COMPOSITIONS

The present invention also relates to pharmaceutical compositions comprising, as an active ingredient, at least one of the compounds of the general formula I or a pharmaceutically acceptable salt thereof and, usually, such compositions also contain a pharmaceutically acceptable carrier or diluent.

Pharmaceutical compositions comprising a compound of the present invention may be prepared by conventional techniques, e.g. as described in Remington: The Science and Practise of Pharmacy, 19$^{th}$ Ed., 1995. The compositions may appear in conventional forms, for example capsules, tablets, aerosols, solutions, suspensions or topical applications.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, syrup, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, topical, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
| --- | --- |
| Active compound (as free compound or salt thereof) | 100 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | |
| Coating: | |
| HPMC approx. | 9 mg |
| *Mywacett 9-40 T approx. | 0.9 mg |

*Acylated monoglyceride used as plasticizer for film coating.

The compounds of the invention may be administered to a mammal, especially a human in need of such treatment, prevention, elimination, alleviation or amelioration of an indication related to all painful, hyperalgesic and/or inflammatory conditions in which C-fibres play a pathophysiological role such as e.g. neurogenic pain, neurogenic inflammation, migraine, neuropathy, itching and rheumatoid arthritis, as well as indications caused by or related to the secretion and circulation of insulin antagonising peptides, such as non-insulin-dependent diabetes mellitus (NIDDM), insulin resistance or ageing-associated obesity. Such mammals include also animals, both domestic animals, e.g. household pets, and non-domestic animals such as wildlife.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, in an effective amount.

The compounds of the invention are effective over a wide dosage range. For example, in the treatment of humans, dosages from about 0.5 to about 1000 mg, preferably from about 1 to about 500 mg of compounds of formula I, conveniently given from 1 to 5 times daily. A most preferable dosage is from about 50 to about 200 mg per dose when administered to e.g. a human. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage form comprising from about 50 to about 200 mg of active ingredient in or together with a pharmaceutically acceptable carrier per unit dosage.

Usually, dosage forms suitable for oral, nasal, pulmonal or transdermal administration comprise from about 0.5 mg to about 1000 mg, preferably from about 1 mg to about 500 mg of the compounds of formula I admixed with a pharmaceutically acceptable carrier or diluent.

Any novel feature or combination of features described herein is considered essential to this invention.

EXAMPLES

The process for preparing compounds of formula I and preparations containing them is further illustrated in the following examples, which, however, are not to be construed as limiting.

Hereinafter, TLC is thin layer chromatography, $CDCl_3$ is deuterio chloroform and $DMSO-d_6$ is hexadeuterio dimethylsulfoxide. The structures of the compounds are confirmed by either elemental analysis or NMR, where peaks assigned to characteristic protons in the title compounds are presented where appropriate. $^1H$ NMR shifts ($\delta_H$) are given in parts per million (ppm). M.p. is melting point and is given in ° C. and is not corrected. Column chromatography was carried out using the technique described by W. C. Still et al, J. Org. Chem. (1978), 43, 2923–2925 on Merck silica gel 60 (Art. 9385). Compounds used as starting materials are either known compounds or compounds which can readily be prepared by methods known per se.

Example 1
3-(3-(10,11-Dihydro-5H-dibenzo[b,f]azepin-5-ylmethyl)-pyrrolidin-1-yl)-propionic acid hydrochloride

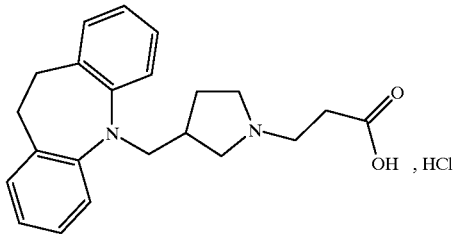

10,11-Dihydro-5H-dibenzo[b,f]azepine (4.88 g, 25 mmol) was added to a stirred suspension of 60% sodium hydride (1.1 g, 27 mmol) in dry N,N-dimethylformamide (15 ml). The mixture was slowly heated to 80° C., maintained at that temperature until the evolution of hydrogen ceased (30 minutes) and cooled to room temperature. A solution of 1-benzyl-3-chloromethylpyrrolidine (5.24 g, 25 mmol, prepared similarly as described in J.Org.Chem., 26, 1519,(1961)) in dry N,N-dimethylformamide (15 ml) was added, followed by sodium iodide (3.75 g, 25 mmol). The mixture was heated at 120° C. for 20 h. The cooled mixture was diluted with toluene (75 ml) and washed with water (4×50 ml), 0.5 N hydrochloric acid (50 ml), saturated sodium hydrogencarbonate (50 ml) and brine (50 ml). The organic phase was dried ($MgSO_4$), filtered, and the solvent evaporated in vacuo. The oily residue (5.6 g) was purified by column chromatography on silica gel using a mixture of toluene, ethyl acetate and triethylamine (30:10:1) as eluent. This afforded 1.37 g (15%) of 5-(1-benzyl-pyrrolidin-3-ylmethyl)-10,11-dihydro-5H-dibenzo[b,f]azepine as an oil.

TLC: $R_f$=0.31 (SiO$_2$: toluene/ethyl acetate/triethylamine= 30:10:1).

A mixture of the above benzyl protected pyrrolidine (1.37 g, 3.6 mmol), 10% palladium on carbon (0.4 g) and ethanol (10 ml) was placed under an atmosphere of hydrogen at 3.5 atm. for 60 h. The reaction mixture was filtered and the solvent was evaporated in vacuo. This afforded 0.78 g (78%) of 5-(pyrrolidin-3-ylmethyl)-10,11-dihydro-5H-dibenzo[b,f]azepine as an oil.

TLC: $R_f$=0.34 (SiO$_2$: dichloromethane/methanol/acetic acid=80:20:1).

A mixture of the above pyrrolidine (0.75 g, 1.9 mmol), 3-bromopropionic acid ethyl ester (0.68 g, 3.8 mmol), potassium carbonate (0.78 g, 5.7 mmol), sodium iodide (0.28 g, 1.9 mmol) and 2-butanone (10 ml) was heated at reflux temperature for 16 h. The reaction mixture was cooled, diluted with toluene (25 ml) and washed with water (3×10 ml). The organic phase was dried (MgSO$_4$), filtered, and the solvent was evaporated in vacuo. The oily residue was purified by column chromatography on silica gel using a mixture of toluene, ethyl acetate and triethylamine (36:4:1) as eluent. This afforded 0.64 g (89%) of 3-(3-(10,11-dihydro-5H-dibenzo[b,f]azepin-5-ylmethyl)-pyrrolidin-1-yl)-propionic acid ethyl ester as an oil.

TLC: $R_f$=0.40 (SiO$_2$: toluene/ethyl acetate/triethylamine= 20:20:1).

The above ester (0.62 g, 1.6 mmol), dissolved in a mixture of ethanol (10 ml) and 2 N sodium hydroxide (2.7 ml) was stirred at room temperature for 16 h. The mixture was diluted with water (15 ml) and the ethanol was evaporated in vacuo. The aqueous solution was adjusted to pH 6 by addition of 2 N hydrochloric acid and extracted with dichloromethane (2×5 ml). The organic phase was dried (MgSO$_4$), filtered and the solvent was removed in vacuo. The residue was dissolved in tetrahydrofuran (2.5 ml) and precipitated by addition of an excess of a solution of hydrogen chloride in ether. The amorphous precipitate was dissolved in tetrahydrofuran (10 ml) and precipitated by addition of ether (50 ml). The solid was isolated by filtration and dried to give 0.44 g (69%) of the title compound as an amorphous solid.

HPLC retention time=17.25 minutes (5 μm C18 4×250 mm column, eluting with a 20–80% gradient of 0.1% trifluoroacetic acid/acetonitrile and 0.1% trifluoroacetic acid/water over 25 minutes at 35° C.).

Calculated for C$_{22}$H$_{26}$N$_2$O$_2$, HCl, 1.25 H$_2$O; C, 64.54%; H, 7.26%; N, 6.84%; Found: C: 64.44%; H: 7.14%; N: 6.57%.

Example 2
(2-(2-(10,11-Dihydro-5H-dibenzo[b,f]azepin-5-ylmethyl)-morpholin-4-yl)-acetic acid hydrogen oxalate

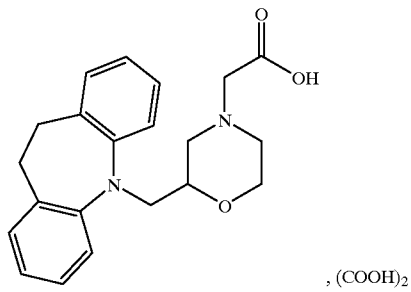

A mixture of 5-(2-morpholinylmethyl)-10,11-dihydro-5H-dibenz[b,f]azepine (1.48 g, 0.005 mol, prepared similarly as described in Ger. Offen. 2,555 351, 1976), ethyl bromoacetate (0.84 g, 0.005 mol), potassium iodide (0.83 g, 0.05 mol) and anhydrous potassium carbonate (2.07 g, 0.015 mol) in 2-butanone (25 ml) was stirred at 70° C. for 7 h. The solid was filtered off, washed with 2-butanone and the filtrates were evaporated in vacuo. The oily residue (2.03 g) was purified by column chromatography on silica gel (40 g) using a mixture of benzene and ethyl acetate (9:1) as eluent. This afforded 1.70 g (89%) of 2-(2-(10,11-dihydrodibenzo[b,f]azepin-5-ylmethyl)morpholin-4-yl)acetic acid ethyl ester as an oil.

TLC: $R_f$=0.48 (SiO$_2$: n-hexane/acetone=2:1)

A mixture of above ester (1.06 g, 0.0028 mol) and 20% sodium hydroxide (1.85 ml) in ethanol (17 ml) was stirred at room temperature for 18 h. Ethanol was evaporated in vacuo, the residue was dissolved in dichloromethane (50 ml), and the mixture was acidified with acetic acid. The organic layer was separated, washed with water (3 ml), dried (MgSO$_4$) and the solvent was evaporated in vacuo. The residue was dissolved in ether (50 ml), the solution was made acidic with a solution of hydrogen chloride in ether and the mixture was stirred for 20 h. The amorphous residue was filtered off and washed with ether. This afforded 0.82 g (76%) of the hydrochloride of the title compound.

The above hydrochloride was suspended in water (5 ml) and alkalised with concentrated ammoniumhydroxide to pH 12. The mixture was acidified to pH 6.5 with acetic acid and extracted with dichloromethane (3×10 ml). The extracts were washed with water (2 ml), dried (MgSO$_4$) and evaporated in vacuo. The residue (0.55 g, 1.55 mmol) was dissolved in acetone (3 ml) and neutralised with a solution of oxalic acid dihydrate (0.36 g, 1.55 mmol) in acetone (3 ml). The precipitated salt was filtered off, washed with acetone (2×3 ml) and dried. This afforded 0.55 g of the title compound.

M.p. 195–199° C.; Calculated for C$_{21}$H$_{24}$N$_2$O$_3$, C$_2$H$_2$O$_4$, 0.5 H$_2$O: C, 61.19%; H, 6.03%; N, 6.20%; Found: C, 61.25%; H, 5.80%; N, 6.13%.

Example 3
(3-(10,11-Dihydro-5H-dibenz[b,f]azepin-5-ylmethyl)-1-piperidyl)acetic acid acetate

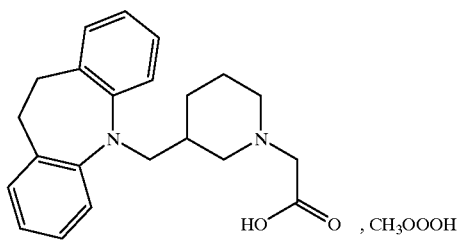

A mixture of 1-benzyl-3-piperidinecarbonyl chloride hydrochloride (12.5 g, 45.6 mmol), 10,11-dihydro-5H-dibenz[b,f]azepine (8.9 g, 45.6 mmol), N,N-dimethylaniline (15 ml) and toluene (100 ml) was heated at reflux temperature for 14 h. The mixture was decanted and to the remaining solid 10% ammonia (100 ml) and chloroform (100 ml) were added. The phases were separated and the combined toluene and chloroform phases were dried (K$_2$CO$_3$) and evaporated in vacuo. The residue was purified by gradient chromatography on silica gel (200 g) using benzene and chloroform as eluents. The chloroform fractions afforded the crude product. This was dissolved in ethanol (30 ml) and neutralised with oxalic acid in acetone, affording 8.8 g (39%) of 3-(10,11-dihydro-5H-dibenz[b,f]azepin-5-ylcarbonyl)-1-benzylpiperidine hydrogen oxalate hemihydrate.

The free base (7.0 g, 17.65 mmol) was released from the above oxalate using aqueous ammonia, and extracted with dichloromethane. The solvent was evaporated and the residue was dissolved in tetrahydrofuran (60 ml). After addition of sodium borohydride (1.25 g) the mixture was stirred for 30 minutes and a solution of boron trifluoride ethyl etherate (5.4 g) in tetrahydrofuran (20 ml) was added dropwise. The mixture was stirred for 5 h at room temperature, 20% hydrochloric acid (40 ml) was added and the mixture was heated at reflux temperature for 7 h. The mixture was made alkaline with 20% sodium hydroxide and extracted with benzene (3×30 ml). The organic phase was dried ($K_2CO_3$) and the solvent was evaporated in vacuo. The residue was purified by chromatography on silica gel (100 g) using chloroform as eluent. This afforded 6.0 g of crude 3-(10,11-dihydro-5H-dibenz[b,f]azepin-5-ylmethyl)-1-benzylpiperidine.

TLC : $R_f$=0.36 ($SiO_2$: chloroform/ethanol/ammonia= 30:1:0.05)

The above protected piperidine (5.9 g, 15.4 mmol) was dissolved in methanol (100 ml), 10% Pd/C (4.0 g) suspended in toluene (15 ml) was added and the mixture was hydrogenated at 30° C. at 5 MPa. The catalyst was filtered off and methanol was evaporated in vacuo. The residue was purified by gradient chromatography on silica gel (50 g) using first chloroform and then ethanol as eluents. This afforded 2.3 g (70%) of 3-(10,11-dihydro-5H-dibenz[b,f]azepin-5-ylmethyl)piperidine.

TLC: $R_f$=0.07 ($SiO_2$: chloroform/ethanol/ammonia= 20:2:0.1)

A mixture of the above piperidine (2.05 g, 7 mmol), ethyl bromoacetate (1.36 g, 8.1 mmol), potassium carbonate (1.7 g, 12.3 mmol) and acetone (50 ml) was heated at reflux temperature under stirring for 7 h. The mixture was filtered and the solvent evaporated in vacuo. The oily residue was purified on silica gel (20 g) using ethyl acetate as eluent to give 2.3 g (87%) 3-(10,11-dihydro-5H-dibenz[b,f]azepin-5-ylmethyl)-1-piperidylacetic acid ethyl ester as an oil.

TLC: $R_f$=0.70 ($SiO_2$: chloroform/ethanol/ammonia= 20:1:0.05

The above ester (2.3 g, 6.1 mmol) was dissolved in ethanol (30 ml) and 20% sodium hydroxide (3 ml) was added. The mixture was allowed to stand for 7 days at room temperature, ethanol was evaporated in vacuo and water (20 ml) was added. The mixture was extracted with diethyl ether and the phases were separated. Acetic acid (3 ml) was added to the aqueous phase and the mixture was extracted with dichloromethane (50 ml). The organic phase was dried ($MgSO_4$) and the solvent was evaporated in vacuo. The residue was dissolved in acetone and the formed precipitate was filtered off. This afforded 1.23 g (50%) of the title compound.

M.p. 142–146° C.; Calculated for $C_{22}H_{26}N_2O_2$, $CH_3COOH$: C, 70.22%; H, 7.37%; N, 6.82%; Found: C, 70.37%; H, 7.14%; N, 6.72%.

Example 4

(2-(3-(10,11-Dihydro-5H-dibenz[b,f]azepin-5-yl)-1-propyl)-1-piperidine)acetic acid hydrochloride

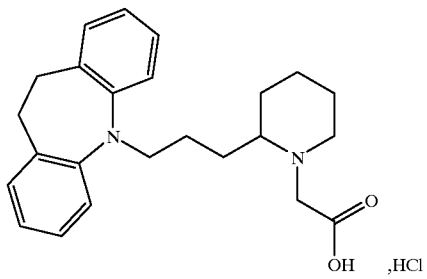

A solution of 3-(2-piperidine)propanol (12.09 g, 0.084 mol, prepared similarly as described in EP 436 199 (1990)) and triethylamine (34.15 g, 0.337 mol) in benzene (240 ml) was cooled to 10° C. and a solution of methanesulfonyl chloride (21.2 g, 0.185 mol) in benzene (40 ml) was added over 0.5 h. The reaction mixture was allowed to warm up to room temperature and stirred for additional 3 h. The solid was filtered off, the filtrate was washed with water (2×100 ml), dried ($MgSO_4$) and evaporated in vacuo. This afforded 14.0 g (73%) of 1-methylsulfonyl-2-(3-methylsulfonyloxypropyl)piperidine, which was used in the next step without purification.

To a solution of iminodibenzyl (6.24 mol, 0.032 mol) in benzene (100 ml) a 50% suspension of sodium amide in toluene (2.2 g, 0.028 mol) was added, and the mixture was stirred at 68–70° C. for 1.5 h. The reaction mixture was partially cooled, the solution of the above methylsulfonyl derivative (9.0 g, 0.03 mol) in benzene (40 ml) was added and the mixture was stirred at 80–90° C. for 15 h. After cooling, the mixture was washed with water (3×100 ml), dried ($MgSO_4$) and evaporated in vacuo. The residue was purified by column chromatography on silica gel (180 g) using benzene and mixtures of benzene and chloroform as eluents, affording 1-methylsulphonyl-2-(3-(10,11-dihydro-5H-dibenz[b,f]azepin-5-yl)-1-propyl)piperidine (9.8 g, 87%).

TLC: $R_f$=0.65 ($SiO_2$: chloroform).

To a solution of the above methanesulphonate (4.17 g, 0.0104 mol) in toluene (25 ml) a solution of sodium dihydrido-bis(2-methoxyethoxy)aluminate (63% solution in toluene, 8.34 g, 0.0417 mol) in toluene (10 ml) was added dropwise over 10 minutes under an argon atmosphere. The reaction mixture was warmed up to 110° C. and then stirred at this temperature for 5 h. After standing overnight, the mixture was quenched with 10% sodium hydroxide (25 ml), dichloromethane (120 ml) was added and the phases were separated. The aqueous phase was extracted with dichloromethane (3×30 ml), and the combined dichloromethane phases were washed with water (30 ml), brine (20 ml), dried ($MgSO_4$) and evaporated in vacuo. The residue was purified by chromatography (100 g) using benzene, chloroform and chloroform saturated with ammonia, gradually, as eluents, affording oily 2-(3-(10,11-dihydro-5H-dibenz[b,f]azepin-5-yl)-1-propyl)piperidine (2.95 g, 88%).

TLC: $R_f$=0.38 ($SiO_2$: chloroform).

A solution of the above piperidine base in diethyl ether (50 ml) was treated with a solution of oxalic acid dihydrate (1.15 g, 9.1 mmol) in ethanol (4 ml). This afforded 3.55 g of the corresponding hydrogen oxalate.

A mixture of the above piperidine (base liberated from hydrogen oxalate, 2.85 g, 0.00883 mol) in 2-butanone (60 ml), ethyl bromoacetate (1.7 g, 0.0102 mol) and potassium carbonate (2.15 g, 0.0155 mol) was stirred at 70–80° C. for 5 h. The reaction mixture was diluted with benzene (60 ml)

and the solid was filtered off, washed with benzene (2×10 ml) and the filtrates were evaporated in vacuo. The residue (3.85 g) was purified by column chromatography on silica gel (100 g) using benzene, a mixture of benzene and chloroform (1:1) and chloroform as eluents, affording 3.25 g (91%) of (2-(3-(10,11-dihydro-5H-dibenz[b,f]azepin-5-yl)-1-propyl)-1-piperidine)acetic acid ethyl ester as an oil.

TLC: $R_f$=0.43 (SiO$_2$: chloroform).

The above base was dissolved in acetone (20 ml) and treated with a solution of oxalic acid dihydrate (1.0 g, 0.008 mol) in acetone (5 ml). Acetone was evaporated and the residue was stirred with diethyl ether (80 ml) for 5 h. Precipitated hydrogen oxalate was filtered off and recrystallised from a mixture of ethanol and diethyl ether. This afforded 2.52 g (63%) of the hydrogen oxalate.

To a solution of the above ester (base liberated from hydrogen oxalate; 2.2 g, 0.0054 mol) in ethanol (14 ml) 15% sodium hydroxide (4.5 ml) was added and the reaction mixture was stirred at the room temperature for 2 h and left standing overnight. The mixture was diluted with dichloromethane (200 ml) and acidified with hydrochloric acid to pH 1. The organic layer was separated and washed with water (5 ml), brine (10 ml), dried (MgSO$_4$) and evaporated in vacuo. The residue was re-evaporated with acetone (3×15 ml) and then stirred with diethyl ether (80 ml) overnight. The precipitated product was filtered off, washed with diethyl ether and dried. This yielded 1.95 g (87%) of the title compound as an amorphous solid.

Calculated for $C_{24}H_{30}N_2O_2$, HCl, ¼ $H_2O$: C, 68.80%; H, 7.46%; N, 6.69%; Cl, 8.46%; Found: C, 68.54%; H, 7.51%; N, 6.42%; Cl, 8.50%.

Example 5
(4-((10,11-Dihydro-5H-dibenz[b,f]azepin-5-yl)methyl)-1-piperidine)propionic acid hydrogen oxalate

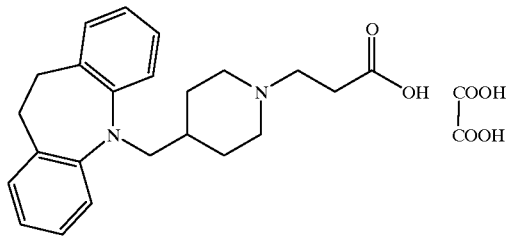

A mixture of 1-benzyl-4-piperidinecarbonylchloride hydrochloride (25.0 g, 91 mmol), 10,11-dihydro-5H-dibenzo[b,f]azepine (17.6 g, 90 mmol), N,N-dimethylaniline (25 ml) and toluene (150 ml) was heated at reflux temperature under stirring for 14 h. The mixture was decanted and to the remaining solid 10% ammonia (100 ml) and chloroform (150 ml) were added. The phases were separated and the combined toluene and chloroform phases were dried (K$_2$CO$_3$) and evaporated in vacuo. The residue was purified by chromatography on silica gel (300 g) using benzene and ethyl acetate as eluents. The crude base was crystallised from cyclohexane, yielding 13.0 g (36%) of 4-((10,11-dihydro-5H-dibenz[b,f]azepin-5-yl)carbonyl)-1-benzylpiperidine.

The above base (10.1 g, 25.5 mmol) was dissolved in tetrahydrofuran (90 ml), sodium borohydride (1.7 g) was added and over a period of 30 minutes, a solution of borontrifluoride etherate (7.4 g) in tetrahydrofuran (30 ml) was added dropwise. The reaction mixture was heated at reflux temperature for 5 h, quenched by addition of 20% hydrochloric acid (50 ml) and heated at reflux temperature for 7 h. The mixture was made alkaline with 20% sodium hydroxide, the product was isolated by extraction with benzene, the organic phase was dried (K$_2$CO$_3$) and the solvent was evaporated in vacuo. The residue was dissolved in diethyl ether and treated with a solution of oxalic acid in acetone yielding 9.3 g (77%) of 4-((10,11-dihydro-5H-dibenz[b,f]azepin-5-yl)methyl)-1-benzylpiperidine hydrogen oxalate The base was librated from the above oxalate using aqueous ammonia, extracting with dichloromethane and evaporating the solvent. The residue was dissolved in a mixture of methanol (40 ml), acetic acid (60 ml) and toluene (20 ml). 10% Pd/C (4.5 g, suspension in toluene) was added and the mixture was hydrogenated at 50° C. and 5 MPa. The catalyst was filtered off and the solvents were evaporated, affording a residue, which was made alkaline using 10% ammonia and extracted with dichloromethane (2×50 ml). The solvent was evaporated and the residue was purified by column chromatography on silica gel (50 g) using chloroform and ethanol as eluents. This afforded 3.0 g (57%) of 4-((10,11-dihydro-5H-dibenz[b,f]azepin-5-yl)methyl)piperidine.

TLC: $R_f$=0.05 (SiO$_2$: chloroform/ethanol/ammonia= 20:2:0.1)

A mixture of the above base (3.0 g, 10.2 mmol), ethyl acrylate (1.1 g, 11 mmol) and ethanol (50 ml) was heated at reflux temperature for 7 h. The mixture was evaporated in vacuo and the remaining solid was recrystallised from ethanol to give 2.6 g (65%) of 4-((10,11-dihydro-5H-dibenz[b,f]azepin-5-yl)methyl)-1-piperidinepropionic acid ethyl ester as crystals.

The above ester (2.4 g, 6.1 mmol) was dissolved in ethanol (40 ml) and 20% sodium hydroxide (4 ml) was added. The mixture was allowed to stand for 7 days at room temperature, ethanol was evaporated in vacuo and water (70 ml) was added. The mixture was extracted with diethyl ether and the phases were separated. Acetic acid (4 ml) was added to the aqueous phase, and the solid was filtered off and recrystallised from aqueous ethanol, to give the hydrate of the title acid. The hydrate (2.24 g, 5.46 mmol) was dissolved in acetone and treated with oxalic acid dihydrate (0.80 g) in acetone. The precipitate was filtered off, washed with acetone and dried, affording 2.23 g (90%) of the title compound.

M.p. 187–189° C.; Calculated for $C_{23}H_{28}N_2O_2$, $C_2H_2O_4$: C, 66.06%; H, 6.65%; N, 6.16%; Found: C, 66.00%; H, 6.39%; N, 5.79%.

What is claimed is:
1. A compound of formula I

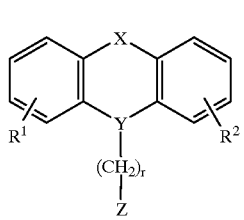

(I)

wherein $R^1$ and $R^2$ independently are hydrogen, halogen, trifluoromethyl, hydroxy, $C_{1-6}$-alkyl or $C_{1-6}$-alkoxy; and Y is >N—CH$_2$— wherein only the underscored atom participates in the ring system; and X is —C(R$^6$R$^7$)—, —CH$_2$CH$_2$—, —CH=CH—CH$_2$—, —CH$_2$—CH=CH—, —CH$_2$—(C=O)—, —(C=O)—CH₂—, —CH₂CH₂CH₂—, —CH=CH—, CH(R¹⁰)CH₂—, —CH₂CH(R¹⁰) or —(C=O)— wherein R⁶ and R⁷ independently are hydrogen or $C_{1-6}$-alkyl and wherein R¹⁰ is $C_{1-6}$-alkyl or phenyl; and r is 0, 1 or 2; and Z is selected from

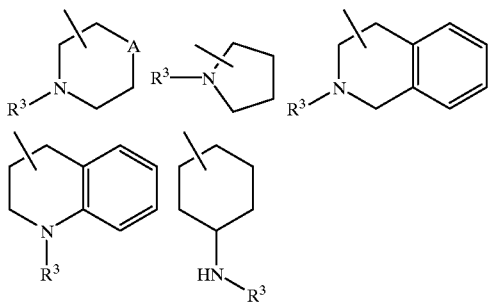

wherein A is —CH₂—, —O—, —S— or —N(R⁵)— wherein R⁵ is H or $C_{1-6}$-alkyl; and
R³ —(CH₂)$_p$COR⁴ wherein p is 1, 2, 3 or 4 and R⁴ is OH, NH₂, NHOH or $C_{1-6}$-alkoxy; or a pharmaceutically acceptable salt thereof.

2. A compound according to claim 1 wherein R¹ and R² independently are hydrogen, halogen, trifluoromethyl or $C_{1-6}$-alkyl.

3. A compound according to claim 1 wherein X is —CH₂CH₂— or —CH=CH—.

4. A compound according to claim 1 wherein Z is selected from

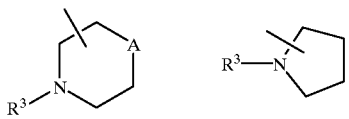

wherein A is —CH₂— or —O—.

5. A compound according to claim 1 wherein R³ is —(CH₂)$_p$COOH wherein p is 1, 2, 3 or 4.

6. A compound according to claim 1 selected from the following:

3-(3-(10,11-Dihydro-5H-dibenzo[b,f]azepin-5-ylmethyl)-pyrrolidin-1-yl)-propionic acid;

(2-(2-(10,11-Dihydro-5H-dibenzo[b,f]azepin-5-ylmethyl)-morpholin-4-yl)-acetic acid;

(3-(10,11-Dihydro-5H-dibenz[(b,f]azepin-5-ylmethyl)-1-piperidyl)acetic acid;

or a pharmaceutically acceptable salt thereof.

7. A compound according to claim 1 selected from the following:

(2-(3-(10,11-Dihydro-5H-dibenz[b,f]azepin-5-yl)-1-propyl)-1-piperidine)acetic acid;

(4-((10,11-Dihydro-5H-dibenz[b,f]azepin-5-yl)methyl)-1-piperidine)propionic acid;

or a pharmaceutically acceptable salt thereof.

8. A method of preparing a compound according to claim 1, comprising:

A) reacting a compound of formula II

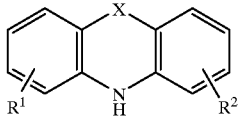

(II)

wherein R¹, R² and X are as defined in claim 1 with a compound of formula III

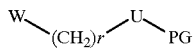

(III)

wherein r is as defined in claim 1, W is a suitable leaving group, PG is a suitable N-protecting group and U is selected from

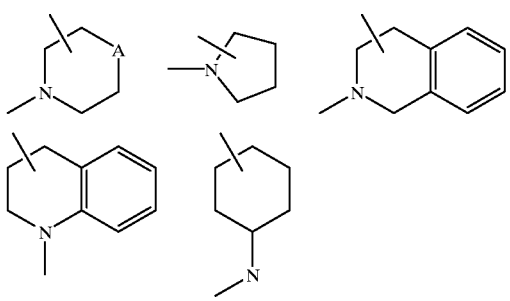

wherein A is as defined in claim 1, to form a compound of formula IV

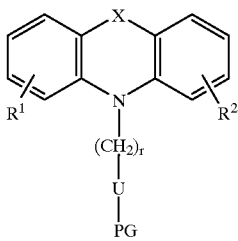

(IV)

wherein the compound of formula IV is N-deprotected to give a compound of formula V

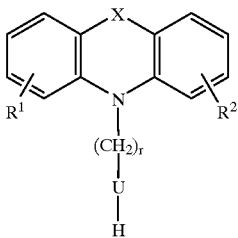

(V)

wherein the compound of formula V is N-alkylated with a compound of formula VI

V—R³   (VI)

wherein R³ is as defined in claim 1 and V is a suitable leaving group, to give the compound of formula I; or B) reacting a compound of formula II

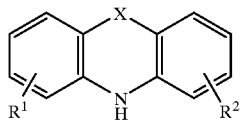
(II)

wherein R¹, R² and X are as defined in claim 1 with a compound of formula VII

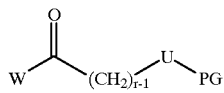
(VII)

wherein r is as defined in claim 1, W is a suitable leaving group, PG is a suitable N-protecting group and U is selected from

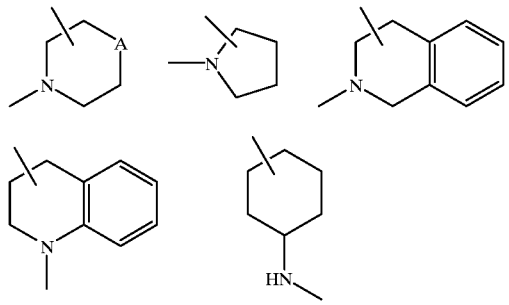

wherein A is as defined in claim 1, to form a compound of formula VIII

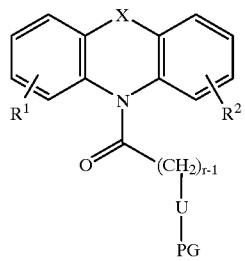
(VIII)

wherein the compound of formula VIII is reduced to give a compound of formula IV

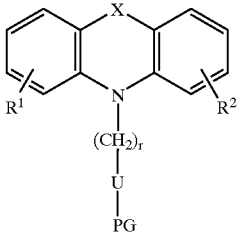
(IV)

wherein the compound of formula IV is N-deprotected to give a compound of formula V

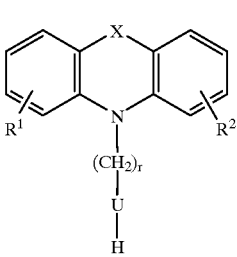
(V)

wherein the compound of formula V is transformed to the compound of formula I as described under A).

9. A pharmaceutical composition comprising as an active component an effective amount of a compound according to claim 1 together with a pharmaceutically carrier or diluent.

10. The pharmaceutical composition according to claim 9 comprising between 0.5 mg and 1000 mg of the compound per unit dose.

11. A method of treating neurogenic pain or inflammation comprising administering to a subject in need thereof an effective amount of a compound according to claim 1.

12. A method of treating neurogenic pain or inflammation comprising administering to a subject in need thereof a pharmaceutical composition according to claim 9.

13. A method of treating neurogenic pain or inflammation associated with neuropathy, rheumatoid arthritis, migraine or itching, comprising administering to a subject in need thereof an effective amount of a compound according to claim 1.

14. A method of treating neurogenic pain or inflammation associated with neuropathy, rheumatoid arthritis, migraine or itching, comprising administering to a subject in need thereof a pharmaceutical composition according to claim 9.

15. A method of treating non-insulin-dependent diabetes mellitus (NIDDM) comprising administering to a subject in need thereof an effective amount of a compound claim 1.

16. A method of treating non-insulin-dependent diabetes mellitus (NIDDM) comprising administering to a subject in need thereof a pharmaceutical composition according to claim 9.

17. A method of treating insulin resistance comprising administering to a subject in need thereof an effective amount of a compound of claim 1.

18. A method of treating insulin resistance comprising administering to a subject in need thereof the pharmaceutical composition of claim 9.

* * * * *

UNITED STATES PATENT AND TRADEMARK OFFICE
CERTIFICATE OF CORRECTION

PATENT NO. : 6,214,816 B1　　　　　　　　　　　　　　　　　　　　　　Page 1 of 1
DATED : April 10, 2001
INVENTOR(S) : Hohlweg et al.

It is certified that error appears in the above-identified patent and that said Letters Patent is hereby corrected as shown below:

Column 21,
Lines 31-41, please delete

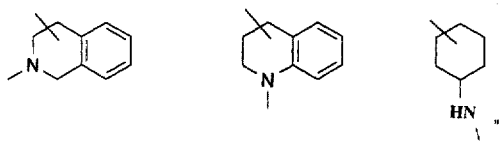

and insert

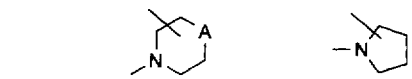

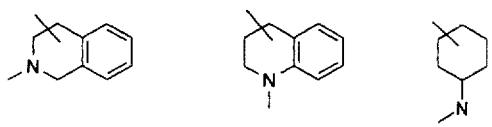

Signed and Sealed this

Twenty-sixth Day of February, 2002

*Attest:*

*Attesting Officer*

JAMES E. ROGAN
*Director of the United States Patent and Trademark Office*